(12) United States Patent
Bachrach

(10) Patent No.: US 6,428,798 B1
(45) Date of Patent: Aug. 6, 2002

(54) BLEMISH EXTRACTION MEANS

(76) Inventor: Lisa Bachrach, 305 Second Ave. No. 523, New York, NY (US) 10003

( * ) Notice: Subject to any disclaimer, the term of this patent is extended or adjusted under 35 U.S.C. 154(b) by 0 days.

(21) Appl. No.: 09/382,074

(22) Filed: Aug. 24, 1999

(51) Int. Cl.$^7$ .......................... A61F 13/00; A61K 9/70; A01N 25/34
(52) U.S. Cl. ....................................................... 424/402
(58) Field of Search ................. 424/402, 443, 424/78.03; 514/859

(56) References Cited

U.S. PATENT DOCUMENTS

| | | | | |
|---|---|---|---|---|
| 3,872,515 A | * | 3/1975 | Miner et al. ................. | 2/168 |
| 4,891,228 A | * | 1/1990 | Thaman et al. ............. | 424/443 |
| 6,106,818 A | * | 8/2000 | Dulog et al. ............. | 424/78.03 |

* cited by examiner

Primary Examiner—Thurman K. Page
Assistant Examiner—S. Howard
(74) Attorney, Agent, or Firm—William L. Paradice, III

(57) ABSTRACT

A blemish extraction means is disclosed which allows for sanitary removal of facial blemishes via force with a reduced risk of inadvertent skin cuts and/or infection. In one embodiment, the blemish extraction means is a sleeve having a reinforced, substantially rigid end portion, and is adapted to be worn over a person's index fingertip. The index fingertip is inserted into the sleeve so that the fingernail tip is in contact with the sleeve's substantially rigid end portion. With a first sleeve on the right hand index finger and a second sleeve on the left hand index finger, a person positions the end portions of the two sleeves on opposite sides of a blemish to be removed, and then firmly presses the respective sleeve end portions towards one another and into the dermis in a pinching fashion so as to push the blemish away from the dermis. Once forced away from the dermis, the blemish is removed using one or both sleeve end portions.

10 Claims, 5 Drawing Sheets

BLEMISH EXTRACTION MEANS

BACKGROUND

1. Field of Invention

This invention relates generally to the extraction of facial blemishes with the intent of improving the cleanliness of blemished skin.

2. Description of Related Art

Acne is a skin disease characterized by facial blemishes such as pimples which are contaminated with bacteria. The disease results from an obstruction of follicle openings on the dermis that leads to the formation of a layer of keratinized cells commonly referred to as whiteheads and/or blackheads. Continued blockage of these follicle openings causes a rupture of the bacteria into the dermis which, in turn, provokes an inflammatory response that leads to the formation of pimples. It is thus desirable to remove the unwanted cell layer (i.e., blackheads) from obstructed follicle openings in order to reduce inflammation and thereby eliminate the pimples.

Acne pads have been known and marketed for several years. Typically, a number of circular acne pads are soaked in a cleansing solution and then applied topically to the acne. The cleansing solution is typically a bactericide such as benzoyl peroxide which removes the unwanted cell layer obstructing the follicle openings by killing the bacteria. Although effective in treating acne, the cleansing solution applied via the acne pads may result in substantial irritation of the skin. Further, acne pads are often insufficient to remove blackheads embedded in the dermis.

Indeed, removing blackheads embedded in the dermis often requires the application of force to the affected area. Typically, two fingernail tips are pressed at complementary angles on opposite sides of the blackhead to pinch the blackhead outwards from the dermis. Although effective in exposing the underlying follicle opening, using one's fingernail tips to remove blackheads may inadvertently and undesirably cut surrounding areas of the dermis. In addition, when using one's fingernail tips to remove blackheads, bacteria and other germs residing under one's fingernails may come into contact with the freshly exposed follicle openings and/or any cuts on the dermis resulting from the pinching action of the fingernail tips.

It would therefore be desirable to be able to remove blackheads without inadvertently cutting and/or infecting the dermis.

SUMMARY

A blemish extraction means is disclosed which allows for sanitary removal of facial blemishes via force with a reduced risk of inadvertent skin cuts and/or infection. In one embodiment, the blemish extraction means is a sleeve having a reinforced, substantially rigid end portion, and is adapted to fit over a person's index fingertip. The index fingertip is inserted into the sleeve so that the fingernail tip is in contact with the sleeve's substantially rigid end portion. With a first sleeve on the right hand index finger and a second sleeve on the left hand index finger, a person positions the respective end portions of the first and second sleeves on opposite sides of a blemish to be removed, and then firmly presses the respective sleeve end portions towards one another and into the dermis in a pinching fashion so as to push the blemish away from the dermis. Once forced away from the dermis, the blemish is removed using one or both sleeve end portions. The sleeve end portion preferably has a textured surface to minimize slippage between the sleeve end portion and the dermis. In some embodiments, the sleeve end portion is soaked in a suitable cleansing solution. In other embodiments, the sleeve end portion is manufactured to contain a suitable anti-bacterial solution.

BRIEF DESCRIPTION OF THE DRAWINGS

Like reference numerals refer to corresponding parts throughout the drawing figures.

DETAILED DESCRIPTION

The present invention is described below with reference to a sleeve illustrated in FIGS. 1–4 for simplicity only. It is to be understood that embodiments of the present invention are equally applicable to other sleeves which, when worn over the fingertips, are used to forcefully remove blemishes from one's dermis. Accordingly, the present invention is not to be construed as limited to specific examples described herein but rather includes within its scope all embodiments defined by the appended claims.

Figure 1:
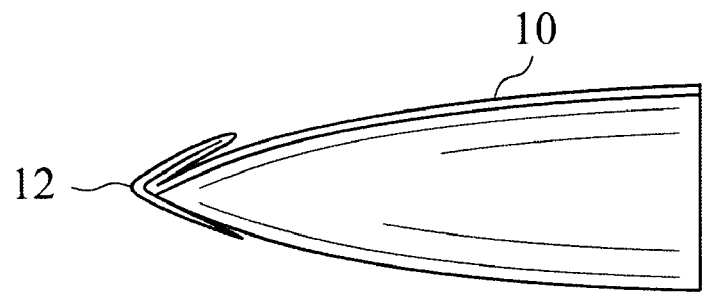
FIG. 1 is a perspective view of a blemish extraction means in accordance with the present invention.
Figure 2:
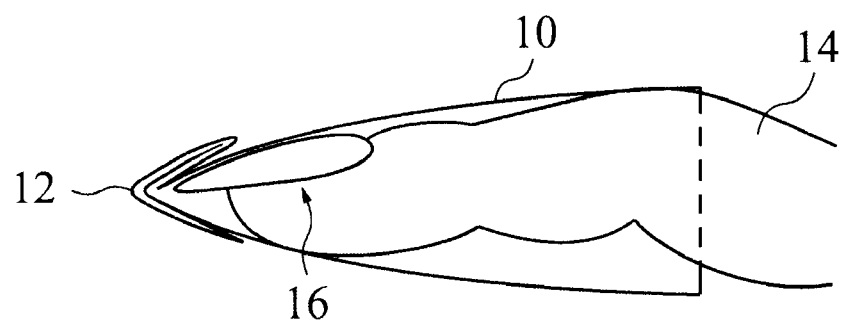
FIG. 2 is a cross-sectional view of the blemish extraction means of FIG. 1 shown encapsulating a finger tip.
Figure 3:
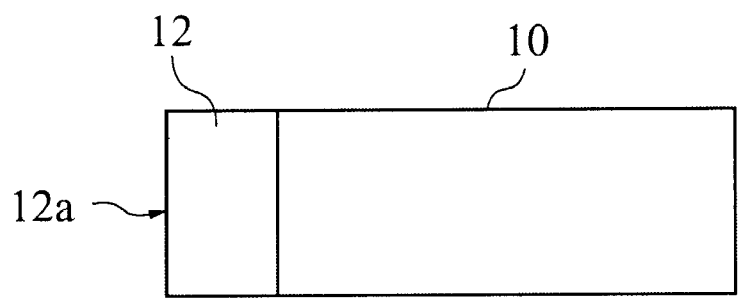
FIG. 3 is a top plan view of the blemish extraction means of FIG. 1.

FIGS. 1–3 show a sleeve 10 for removing blemishes from the dermis. The sleeve 10 is preferably adapted to be worn over a person's index finger and includes a reinforced, substantially rigid end portion 12, although the sleeve 10 may be worn over fingers other than the index finger. When a person's index finger 14 is inserted into the sleeve 10, the fingernail tip 16 should be in contact with the end portion, as illustrated in FIG. 2. Referring to the embodiment shown in FIG. 3, the end portion 12 has a substantially flat edge portion. To remove a blemish using the present invention, a person puts a first sleeve over the right hand index finger and a second sleeve over the left hand index finger, making sure that the fingernail tips 14 are in contact with the respective sleeve end portions 12. The person then positions the index fingers so that the sleeve end portions 12 flank either side of the blemish while gently pressing the respective flat edges 12a of the first and second sleeves 10 against the dermis. The person then firmly presses the respective sleeve end portions 12 towards one another and slightly into the dermis in a pinching fashion to force the blemish away from the dermis. The blemish may then be removed from the dermis using either of the sleeves 10.

Providing the sleeves 10 over the fingertips when forcibly extracting blemishes from the dermis as described above protects the dermis against the sharp edges of one's fingernails, thereby preventing the dermis from being inadvertently cut by the fingernails. In this manner, present embodiments advantageously reduce scarring previously associated with the extraction of blemishes. Further, the sleeves 10 act as a barrier that keeps dirt and germs away from any follicle opening recently exposed by removal of the blemish. If the follicle opening has been damaged by the blemish, the exposed follicle may be especially vulnerable to infection from such dirt and germs. Here, present embodiments are useful in minimizing infection.

The sleeve 10 is preferably made of a hypo-allergenic material. The sleeve end portion 12 is preferably textured so as to grip the dermis surface when it is pressed against the dermis, thereby minimizing slippage between the sleeve end portion 12 and the dermis during removal of blemishes. The edge 12a of the end portion 12 of the sleeve 10 is substantially flat and rigid so that when using the sleeve 10 to remove blemishes, pressure is applied to the dermis in a substantially uniform manner. In this manner, the sleeve 10 maximizes blemish extraction. In some embodiments, the sleeve end portion 12 is soaked in a suitable cleansing solution such as, for instance, an over-the-counter antibacterial agent which further aids treatment of acne. The sleeve 10 is very inexpensive to manufacture, and in some embodiments is discarded after use, thereby leaving nothing to clean up.

Figure 4A:
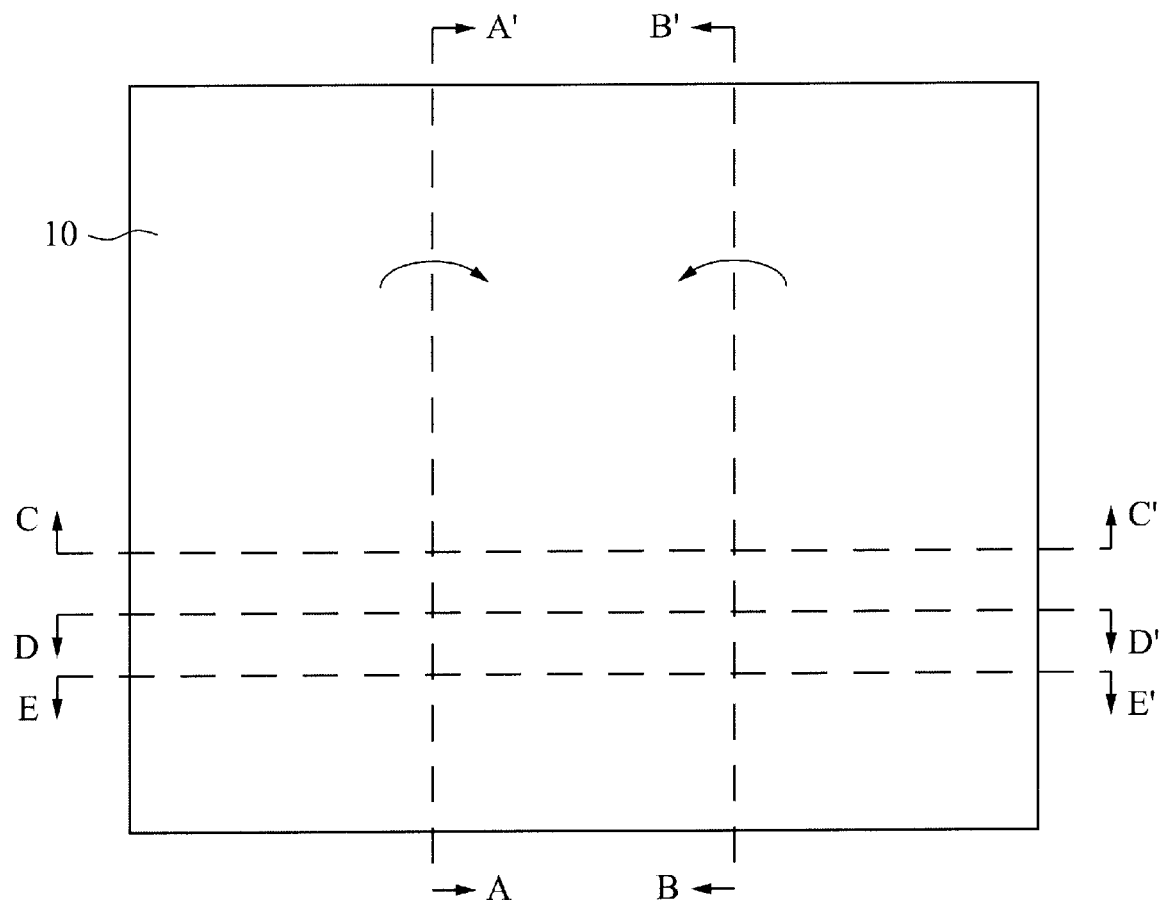
FIGS. 4A–4D illustrate fabrication of one embodiment of the blemish extraction means of FIG. 1.
Figure 4B:
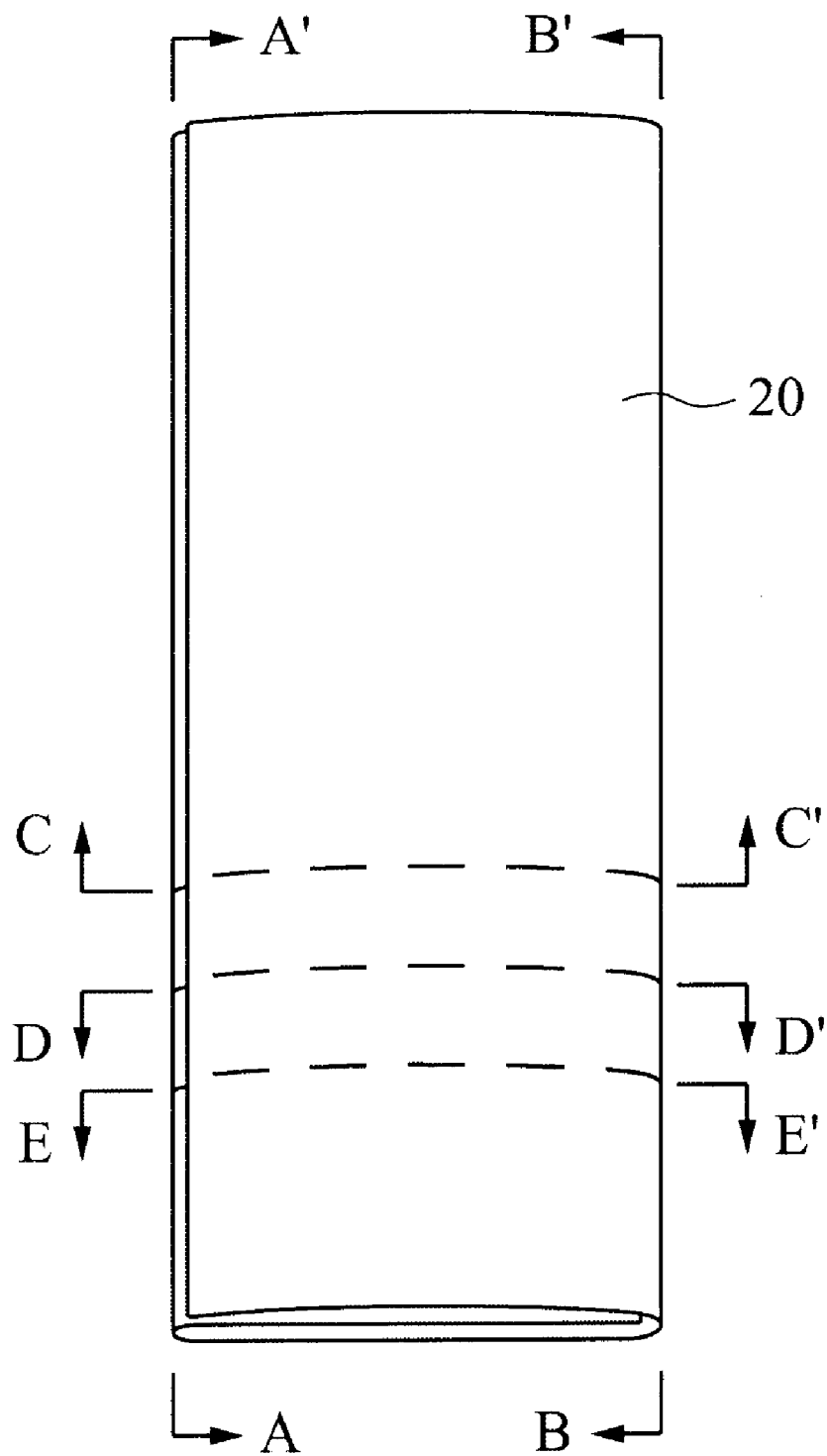
Figure 4C:
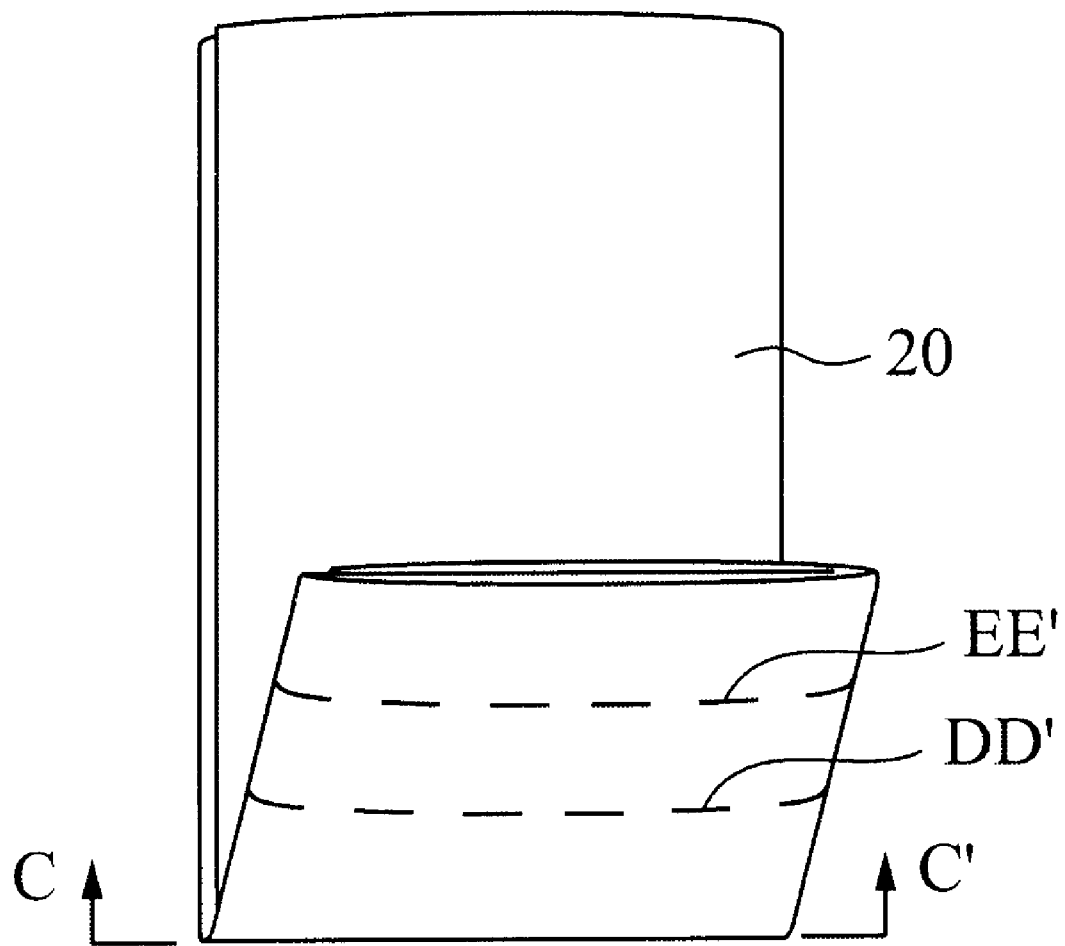
Figure 4D:
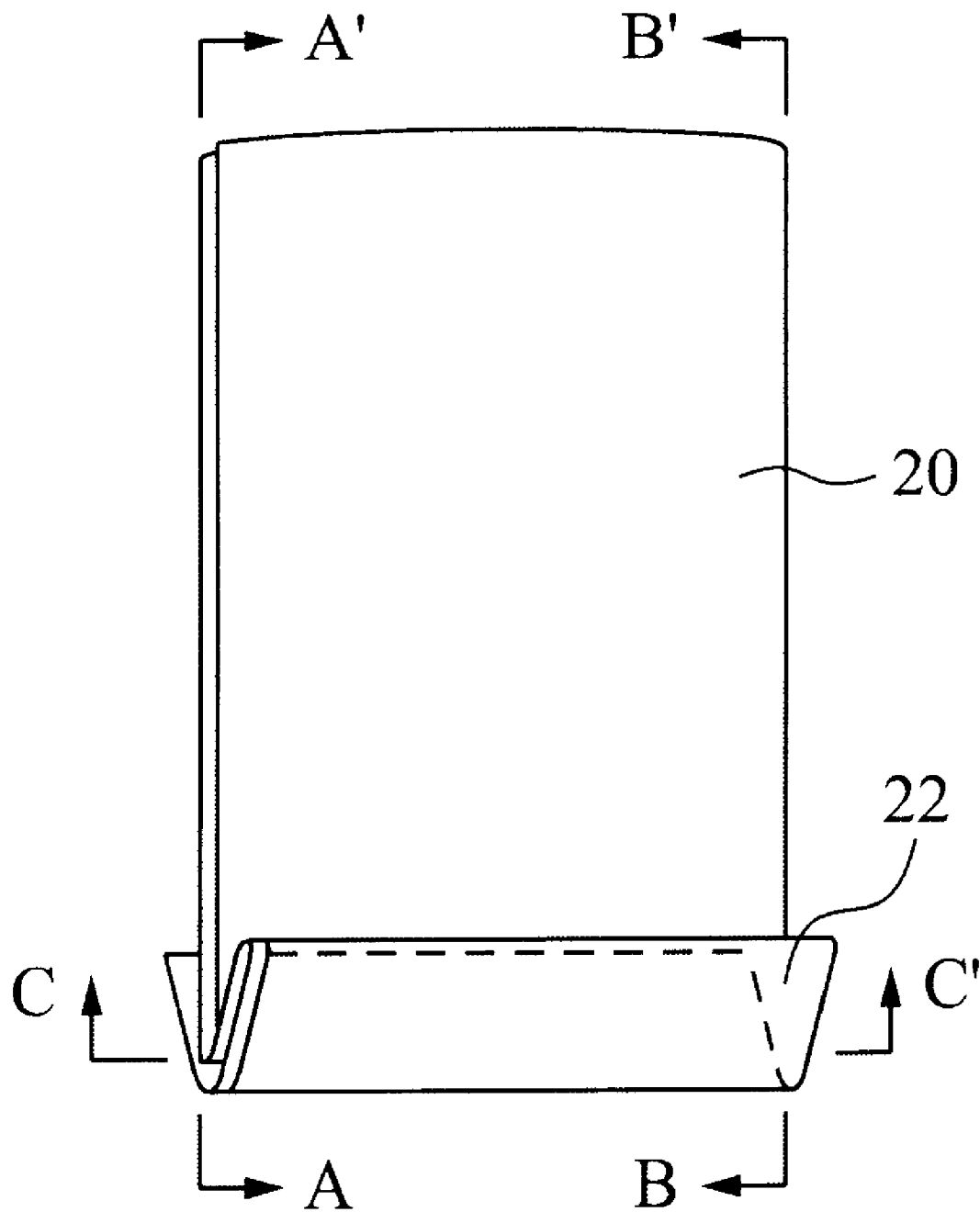

FIGS. 4A–4D illustrates fabrication of the sleeve 10 from a single sheet of material in accordance with one embodiment of the present invention. Referring to FIG. 4A, five fold lines AA', BB', CC', DD', and EE' are provided on a piece of material approximately 2 inches square, although a different size piece of material may be used. The material is first folded along line AA,' and then folded along line BB' to form a sleeve 20, as illustrated in FIG. 4B, where the sleeve 20 is one embodiment of the sleeve 10 of FIGS. 1–3. The sleeve 20 is then folded along line CC', as illustrated in FIG. 4C, and then along lines DD' and EE' to form sleeve end portion 22, as illustrated in FIG. 4D.

While particular embodiments of the present invention have been shown and described, it will be obvious to those skilled in the art that changes and modifications may be made without departing from this invention in its broader aspects and, therefore, the appended claims are to encompass within their scope all such changes and modifications as fall within the true spirit and scope of this invention.

What is claimed is:

1. A sleeve for extracting a blemish from a person's dermis, the sleeve comprising:

an elongated sleeve portion adapted to be fitted over a fingertip of the person; and an end portion having a substantially rigid and substantially flat edge for applying pressure to the dermis on opposite sides of the blemish.

2. The sleeve of claim 1, wherein the end portion comprises a textured material for griping the dermis so as to minimize slippage between the end portion and the dermis when removing the blemish from the dermis.

3. The sleeve of claim 1, wherein the end portion is pre-soaked in a cleansing solution.

4. The sleeve of claim 1, wherein the cleansing portion comprises benzoyl peroxide.

5. A method of removing a blemish from a person's dermis, comprising:

providing first and second elongated sleeves, each having an end portion with a substantially rigid and flat edge;

inserting a finger of the person's left hand into the first elongated sleeve;

inserting a finger of the person's right hand into the second elongated sleeve;

positioning the end portions of the first and second elongated sleeves on either side of the blemish; and pressing the end portions of the first and second sleeves towards one another and into the dermis in a pinching manner, thereby pushing the blemish away from the dermis.

6. The method of claim 5, further comprising:

soaking the end portions of the first and second elongated sleeves in a cleaning solution.

7. The method of claim 6, wherein the cleansing portion comprises benzoyl peroxide.

8. The method of claim 6, further comprising:

removing the blemish from the dermis using the elongated sleeves.

9. The method of claim 6, wherein the fingers comprise index fingers.

10. The method of claim 6, wherein the end portion comprises a textured material for griping the dermis so as to minimize slippage between the end portion and the dermis when removing the blemish from the dermis.

* * * * *